US010226573B2

(12) United States Patent
Baek et al.

(10) Patent No.: US 10,226,573 B2
(45) Date of Patent: Mar. 12, 2019

(54) FLUID OCCLUSION DETECTION APPARATUS AND METHOD

(71) Applicant: Samsung Electronics Co., Ltd., Suwon-si (KR)

(72) Inventors: In-geol Baek, Icheon-si (KR); Young-hyun Kim, Suwon-si (KR); Jae-kyung Kwak, Ansan-si (KR); Sang-hun Lee, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 130 days.

(21) Appl. No.: 14/908,685

(22) PCT Filed: Jul. 28, 2014

(86) PCT No.: PCT/KR2014/006861
§ 371 (c)(1),
(2) Date: Jan. 29, 2016

(87) PCT Pub. No.: WO2015/016547
PCT Pub. Date: Feb. 5, 2015

(65) Prior Publication Data
US 2016/0184517 A1    Jun. 30, 2016

(30) Foreign Application Priority Data

Jul. 30, 2013 (KR) ........................ 10-2013-0090439

(51) Int. Cl.
*A61M 5/142* (2006.01)
*A61M 5/168* (2006.01)

(52) U.S. Cl.
CPC .... *A61M 5/16859* (2013.01); *A61M 5/14244* (2013.01); *A61M 5/16854* (2013.01);
(Continued)

(58) Field of Classification Search
CPC .......... A61M 5/16859; A61M 5/14244; A61M 5/16854; A61M 2005/16863;
(Continued)

(56) References Cited

U.S. PATENT DOCUMENTS 4,369,780 A    1/1983 Sakai
4,373,525 A *  2/1983 Kobayashi ........ A61M 5/14228
                                                128/DIG. 12
(Continued)

OTHER PUBLICATIONS

Notification of International International Search Report, International Search Report and Written Opinion of the International Searching Authority, or the Declaration, dated Nov. 5, 2014 corresponding to International application No. PCT/KR2014/006861.

*Primary Examiner* — Nathan R Price
*Assistant Examiner* — Dung T Ulsh
(74) *Attorney, Agent, or Firm* — Nixon & Vanderhye P.C.

(57) ABSTRACT

A fluid occlusion detection apparatus is disclosed. The fluid occlusion detection apparatus includes: a structure disposed on a fluid delivery device and that is deformed according to pressure; and a change detection sensor in a surrounding region of the structure, wherein the fluid delivery device includes a fluid reservoir container and/or a fluid delivery passageway for connecting a human body and the fluid reservoir container, and the change detection sensor detects a change in a value related to the change detection sensor due to deformation of a shape of the structure according to an increase in pressure inside the fluid delivery device by fluid occlusion inside the fluid delivery device.

7 Claims, 7 Drawing Sheets

(52) U.S. Cl.
CPC ............. *A61M 2005/16863* (2013.01); *A61M 2005/16868* (2013.01); *A61M 2205/0294* (2013.01); *A61M 2205/3306* (2013.01); *A61M 2205/3317* (2013.01)

(58) Field of Classification Search
CPC ........... A61M 2005/16868; A61M 2205/0294; A61M 2205/3306; A61M 2205/3317
See application file for complete search history.

(56) References Cited

U.S. PATENT DOCUMENTS

| | | | | |
|---|---|---|---|---|
| 4,521,186 A * | 6/1985 | Wodlinger | ............. | A61C 19/05 433/71 |
| 4,690,673 A * | 9/1987 | Bloomquist | .......... | A61M 5/142 128/DIG. 12 |
| 4,762,518 A | 8/1988 | Kreinick | | |
| 5,720,721 A * | 2/1998 | Dumas | ............... | A61M 5/16854 604/118 |
| 6,149,394 A * | 11/2000 | Allen | .................. | F04B 43/1253 417/63 |
| 6,423,035 B1 * | 7/2002 | Das | ..................... | A61M 5/1456 128/DIG. 1 |
| 7,875,004 B2 | 1/2011 | Yodfat et al. | | |
| 7,887,505 B2 | 2/2011 | Flaherty | | |
| 8,397,578 B2 * | 3/2013 | Miesel | .................. | G01L 9/0072 604/891.1 |
| 2003/0167035 A1 | 9/2003 | Flaherty et al. | | |
| 2005/0178206 A1 | 8/2005 | Malmstrom et al. | | |
| 2006/0241506 A1 * | 10/2006 | Melker | .................... | A61B 5/08 600/529 |
| 2007/0078377 A1 * | 4/2007 | Mason | ................ | A61M 1/0058 604/27 |
| 2007/0219480 A1 * | 9/2007 | Kamen | ................ | G05D 7/0647 604/20 |
| 2008/0053452 A1 * | 3/2008 | Brown | ............. | A63B 21/00196 128/207.12 |
| 2008/0294094 A1 * | 11/2008 | Mhatre | ............... | A61M 5/1413 604/65 |
| 2009/0053085 A1 * | 2/2009 | Thompson | .......... | A61M 5/1413 417/477.2 |
| 2009/0240118 A1 * | 9/2009 | Aggarwal | ............ | A61B 5/0002 600/301 |
| 2010/0100052 A1 * | 4/2010 | Eckhardt | ................. | A61M 5/14 604/181 |
| 2010/0125288 A1 * | 5/2010 | Gelfand | ............... | A61B 5/0215 606/158 |
| 2010/0234809 A1 * | 9/2010 | Kenley | ............... | A61M 39/281 604/180 |
| 2011/0118662 A1 | 5/2011 | Mhatre et al. | | |
| 2011/0257496 A1 * | 10/2011 | Terashima | ......... | A61B 5/14532 600/347 |
| 2012/0123230 A1 * | 5/2012 | Brown | .............. | A61M 5/16804 600/316 |
| 2012/0132525 A1 * | 5/2012 | Liu | ..................... | C07F 15/0026 204/403.14 |
| 2012/0203179 A1 * | 8/2012 | Hills | ..................... | A61M 5/16831 604/151 |
| 2013/0060194 A1 * | 3/2013 | Rotstein | ............. | A61M 5/1413 604/151 |
| 2013/0107267 A1 * | 5/2013 | Leuenberger | ..... | A61M 5/16854 356/445 |
| 2014/0007694 A1 * | 1/2014 | Geipel | ............. | A61M 5/16854 73/705 |
| 2014/0114238 A1 * | 4/2014 | Lee | ..................... | A61M 5/1456 604/67 |
| 2014/0127795 A1 * | 5/2014 | Dancu | .................... | G01N 21/47 435/289.1 |
| 2015/0064036 A1 * | 3/2015 | Eberhard | ............... | F04B 7/0007 417/557 |
| 2015/0209511 A1 * | 7/2015 | Momose | ............... | A61M 5/145 604/500 |
| 2015/0374903 A1 * | 12/2015 | Muto | ................ | A61M 5/14228 604/151 |

\* cited by examiner

[Fig. 1a]
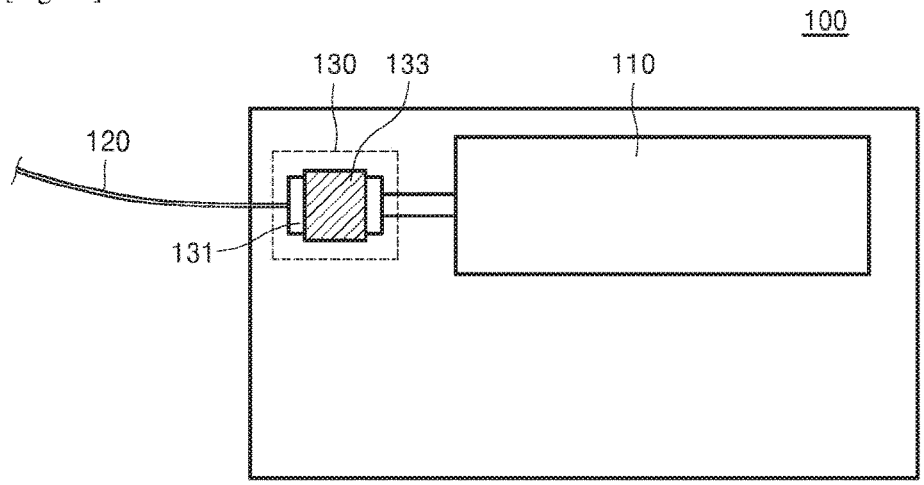
[50] The structure 131 is disposed on the fluid delivery device 100 and may be deformed according to pressure. For example, the structure 131 may be at least one selected from the group consisting of a membrane, a tube, a piston, and a bellows but is not limited thereto.
[Fig. 1b]
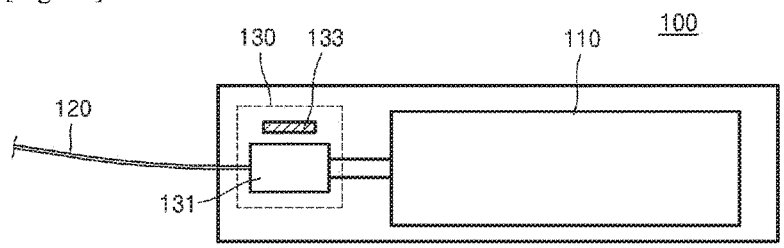
[Fig. 2a]
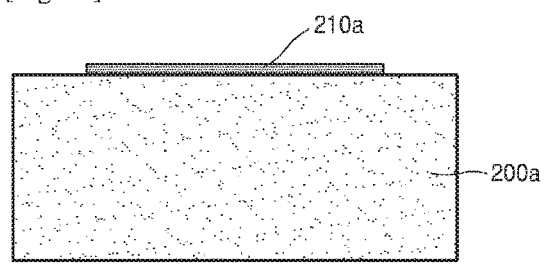
[Fig. 2b]
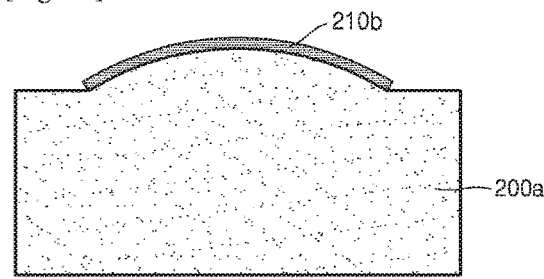

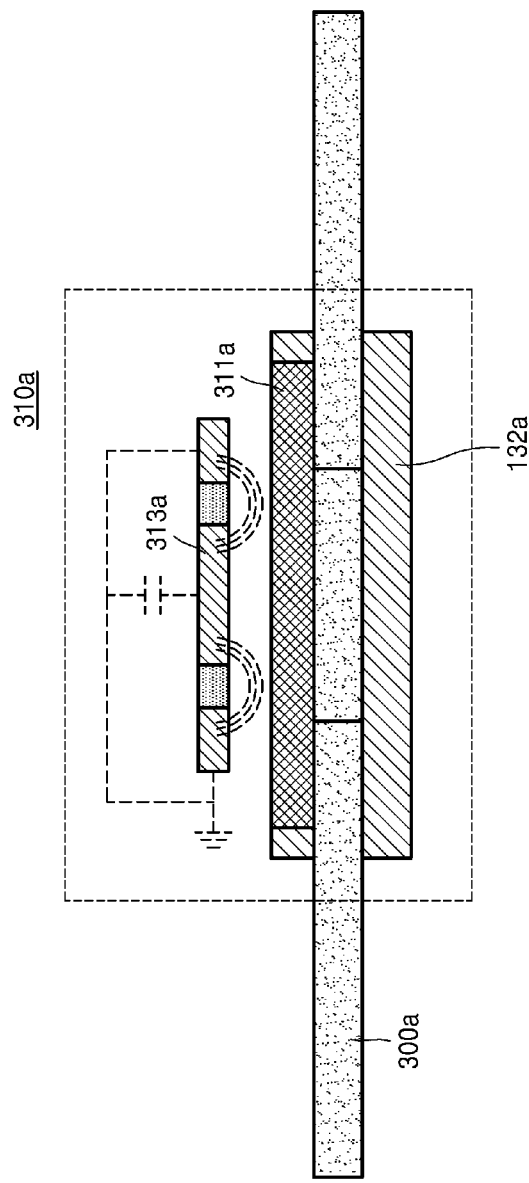
[Fig. 3a]

[Fig. 3b]
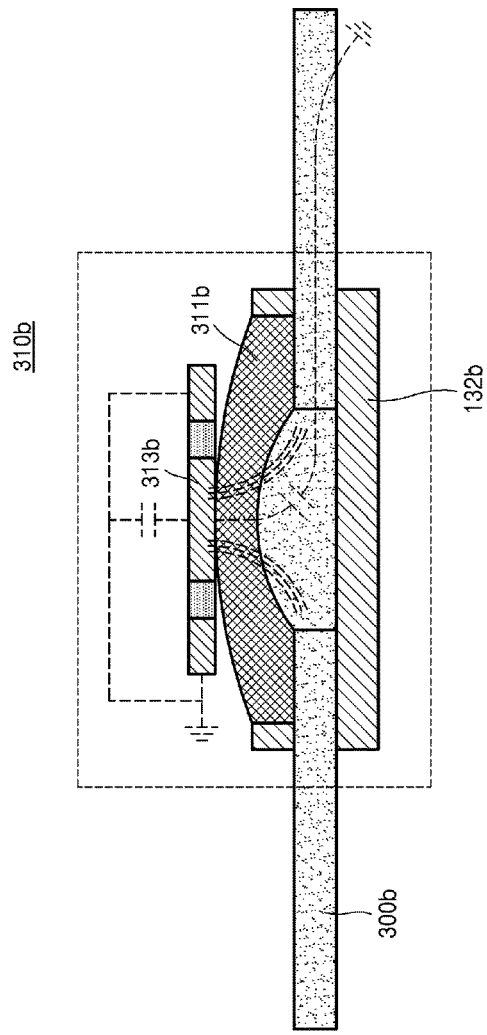
[Fig. 4a]
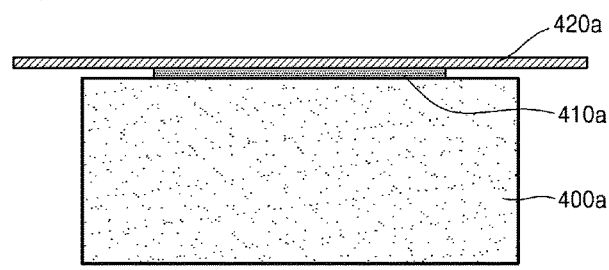
[Fig. 4b]
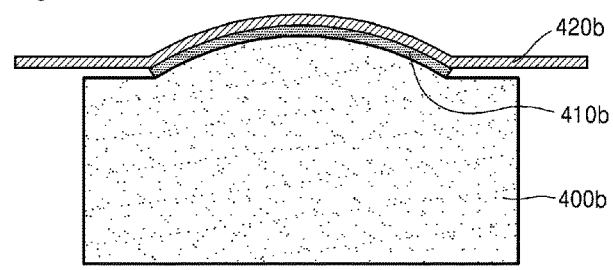

[Fig. 4c]
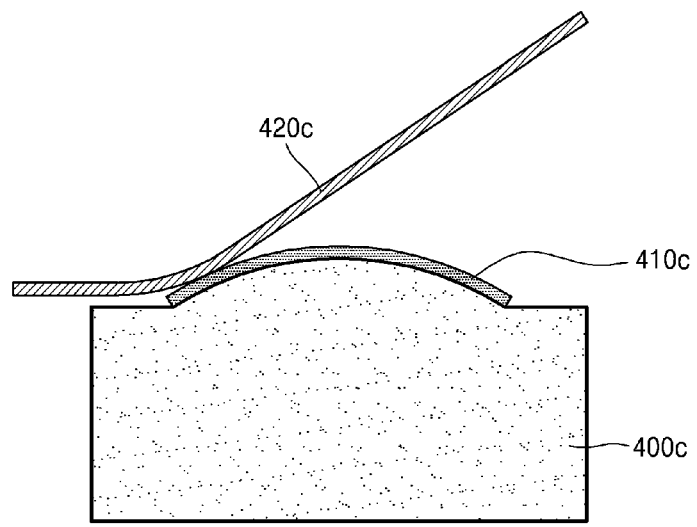
[Fig. 5a]
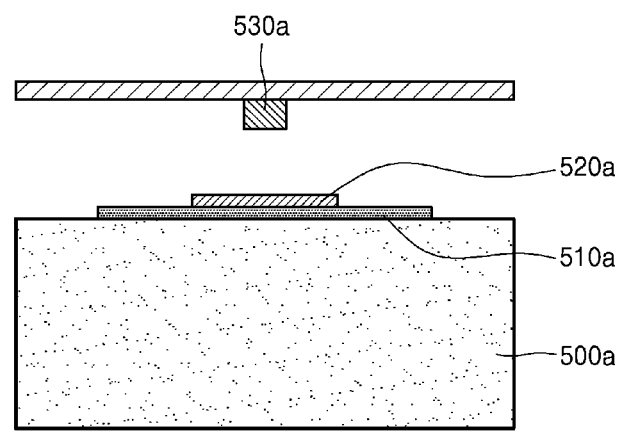
[Fig. 5b]
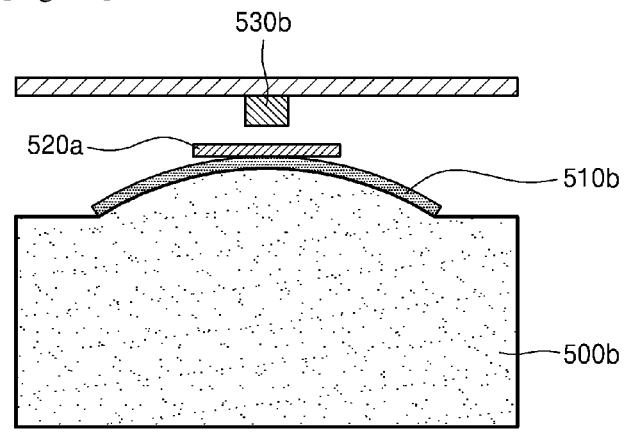

[Fig. 6a]
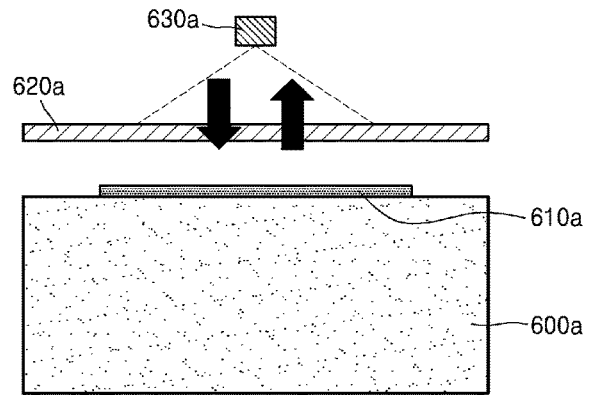
[Fig. 6b]
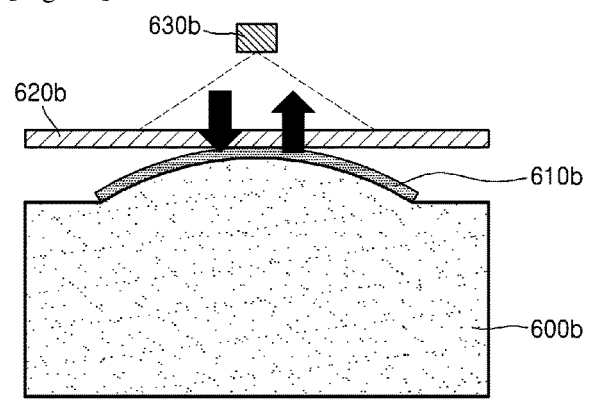
[Fig. 7a]
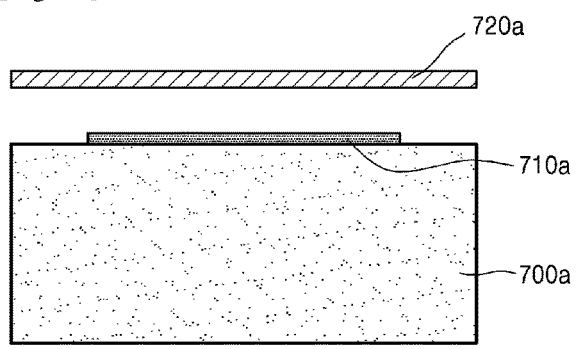
[Fig. 7b]
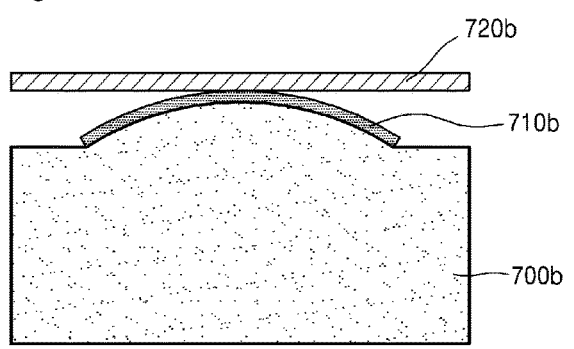

[Fig. 8a]
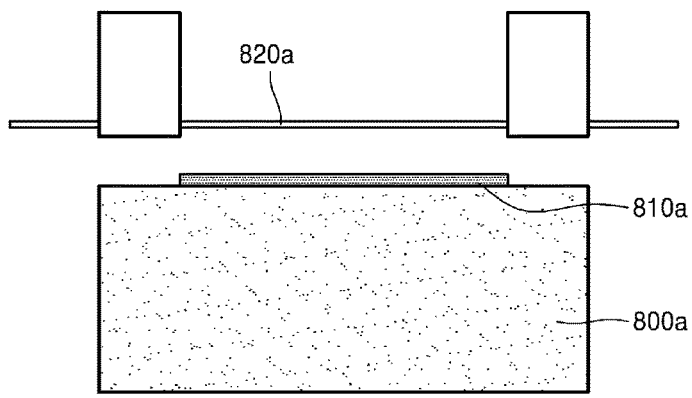
[Fig. 8b]
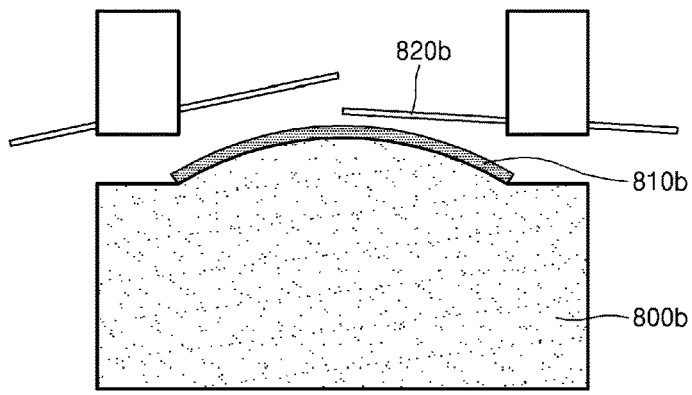
[Fig. 9a]
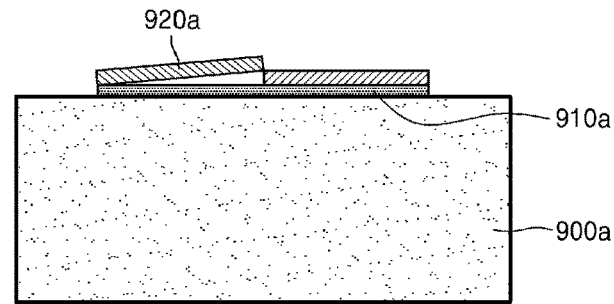
[Fig. 9b]
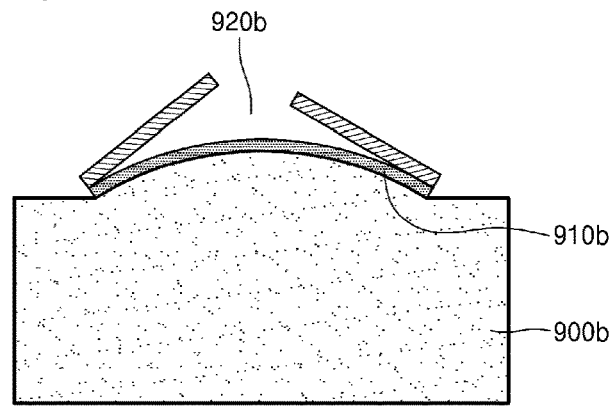

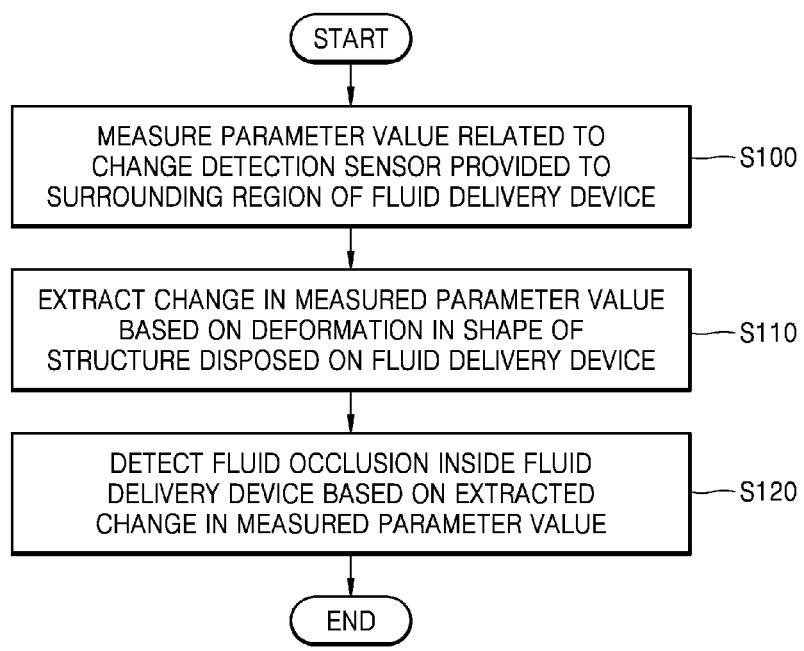

FLUID OCCLUSION DETECTION APPARATUS AND METHOD

TECHNICAL FIELD

One or more embodiments of the present invention relate to fluid occlusion detection apparatuses and methods.

BACKGROUND ART

A diabetic does not normally secrete insulin in his/her body, and thus, it is recommended that the diabetic periodically measures a blood sugar level and directly injects insulin into his/her body. As a method of directly injecting insulin into a diabetic, there are a self-injection method in which an individual voluntarily injects insulin and an automated method in which an insulin pump automatically injects insulin. For the insulin pump, a tube referred to as a needle or a cannula is injected up to a subcutaneous fat layer in order to automatically inject insulin into a body.

In this case, occlusions occur occasionally since protein or fat tissue is stuck to the end of the needle or cannula according to a defense mechanism against foreign substances coming into the body from the outside.

When a force is continuously applied by a piston, a plunger, or a pump to push drugs in an occlusion state, internal pressure of a syringe, a cartridge, and a reservoir increases, and when this phenomenon is continued, if the pressure exceeds a critical value, an occluded portion is forcibly broken, thereby injecting much insulin into the body in a short time.

In this case, due to the sudden insulin injection, a diabetic may be physically damaged, or in a severe case, the diabetic may die due to hypoglycemic shock, and thus, the necessity of quickly and accurately detecting insulin occlusion inside a fluid delivery device, such as a needle or a cannula, has increased.

When a light-emitting diode (LED) device is used in an existing apparatus for detecting fluid occlusion, there is used a method of estimating the occurrence of occlusion according to a change in the intensity of light received by a photo detector due to shape deformation of a reflective film when pressure inside a fluid reservoir device increases. However, In this case, since the LED device is used, it is difficult to continuously measure due to current consumption, and occlusion detection and a detection time varies according to a measurement period. In addition, since external light is necessarily blocked, mechanical complexity increases and many electronic parts and elements are used.

In addition, there is another existing method of detecting occlusion by disposing a conductor on a membrane expanding in response to pressure at a point through which fluid flows and allowing the conductor to function as a switch when electrified through the conductor contacting two electrodes of an upper plate due to swelling of the membrane. However, in this case, occlusion is detected when electrified, but since a pump circuit for injecting the fluid into a human body is still activated, an additional process for stopping injecting the fluid into the human body as soon as detecting occlusion is demanded.

DISCLOSURE OF INVENTION

Solution to Problem

According to one or more embodiments of the present invention, a fluid occlusion detection apparatus includes: a structure disposed on a fluid delivery device and that is deformed according to pressure; and a change detection sensor on a surrounding region of the structure, wherein the fluid delivery device includes a fluid reservoir container and/or a fluid delivery passageway for connecting a human body and the fluid reservoir container, and the change detection sensor detects a change in a value related to the change detection sensor due to deformation of a shape of the structure according to an increase in pressure inside the fluid delivery device by fluid occlusion inside the fluid delivery device.

Advantageous Effects of Invention

One or more embodiments of the present invention include a fluid occlusion detection apparatus and method for decreasing current consumption by using any one of a capacitor, a resistor, a conductor, a magnetic body, a reflective film, and a piezo panel instead of using an existing LED device to detect fluid occlusion.

One or more embodiments of the present invention include a fluid occlusion detection apparatus and method for preventing an inflow of fluid into a human body by supplying power to a pump circuit in a normal state and cutting off power to the pump circuit as soon as fluid occlusion is detected without a separate additional circuit.

BRIEF DESCRIPTION OF DRAWINGS

FIGS. 1A and 1B illustrate a fluid occlusion detection apparatus according to an embodiment of the present invention;

FIGS. 2A and 2B illustrate deformation in a shape of a structure due to an increase in pressure inside a fluid delivery device according to an embodiment of the present invention;

FIGS. 3A and 3B illustrate a change detection sensor including a capacitor, according to an embodiment of the present invention;

FIGS. 4A to 4C illustrate a change detection sensor including a resistor, according to another embodiment of the present invention;

FIGS. 5A and 5B illustrate a change detection sensor including a magnetic body, according to another embodiment of the present invention;

FIGS. 6A and 6B illustrate a change detection sensor including a reflective film, according to another embodiment of the present invention;

FIGS. 7A and 7B illustrate a change detection sensor including a piezo panel, according to another embodiment of the present invention;

FIGS. 8A to 9B illustrate a change detection sensor including a conductor, according to other embodiments of the present invention;

FIG. 10 is a flowchart of a fluid occlusion detection method according to an embodiment of the present invention.

BEST MODE FOR CARRYING OUT THE INVENTION

The structure may be disposed on the fluid reservoir container and/or the fluid delivery passageway for connecting the human body and the fluid reservoir container.

The structure may be at least one selected from the group consisting of a membrane, a tube, a piston, and a bellows.

The change detection sensor may include a capacitor located on the surrounding region of the structure and detect a change in a capacitance of the capacitor when the structure of which the shape has been deformed due to an increase in the pressure inside the fluid delivery device by fluid occlusion inside the fluid delivery device contacts one side of the capacitor.

The change detection sensor may include a resistor disposed on the structure and that may detect a change in a resistance of the resistor when a shape of the resistor is deformed by the structure of which the shape has been deformed due to an increase in the pressure inside the fluid delivery device by fluid occlusion inside the fluid delivery device.

The change detection sensor may include a magnetic body disposed on the structure and a magnetic field sensor for measuring a magnetic field of a surrounding region of the magnetic body, and the magnetic field sensor may detect a change in the magnetic field when a distance between the magnetic body and the magnetic field sensor varies due to deformation of the shape of the structure according to an increase in the pressure inside the fluid delivery device by fluid occlusion inside the fluid delivery device.

The magnetic field sensor may be a Hall effect sensor and/or a lead switch.

The change detection sensor may include, in the surrounding region of the structure, a detection unit including a light-transmitting unit and a light-receiving unit and a reflective film interposed between the structure and the detection unit and that may detect a change in the intensity of light received by the light-receiving unit when the structure of which the shape has been deformed due to an increase in the pressure inside the fluid delivery device by fluid occlusion inside the fluid delivery device contacts the reflective film.

The change detection sensor may include, in the surrounding region of the structure, a piezo panel vibrating at a constant frequency and that may detect a change in the frequency of the piezo panel when the structure of which the shape has been deformed due to an increase in the pressure inside the fluid delivery device by fluid occlusion inside the fluid delivery device contacts one side of the piezo panel.

The change detection sensor may include a conductor in the surrounding region of the structure and detect a change in a current when the conductor is open-circuited according to deformation of the shape of the structure due to an increase in the pressure inside the fluid delivery device by fluid occlusion inside the fluid delivery device.

The conductor may be formed on a carbon bar and/or a ceramic bar and have conductivity.

According to one or more embodiments of the present invention, a fluid occlusion detection method includes: measuring a parameter value related to a change detection sensor provided to a surrounding region of a fluid delivery device; extracting a change in the measured parameter value based on deformation in a shape of a structure disposed on the fluid delivery device; and detecting fluid occlusion inside the fluid delivery device based on the extracted change in the measured parameter value, wherein the fluid delivery device includes a fluid reservoir container and/or a fluid delivery passageway for connecting a human body and the fluid reservoir container, and a shape of the structure is deformed due to an increase in pressure inside the fluid delivery device by the fluid occlusion inside the fluid delivery device.

The structure may be at least one selected from the group consisting of a membrane, a tube, a piston, and a bellows.

The parameter value related to the change detection sensor may be a capacitance of a capacitor provided to the change detection sensor, and a change in the capacitance of the capacitor may be extracted when the structure contacts one side of the capacitor based on the shape deformation of the structure disposed on the fluid delivery device.

The parameter value related to the change detection sensor may be a resistance of a resistor provided to the change detection sensor, and a change in the resistance of the resistor may be extracted when a shape of the resistor disposed on the structure is deformed based on the shape deformation of the structure disposed on the fluid delivery device.

The parameter value related to the change detection sensor may be a magnetic field of a magnetic body provided to the change detection sensor, and a change in the magnetic field of the magnetic body may be extracted when a distance between the magnetic body and a magnetic field sensor for measuring a magnetic field in a surrounding region of the magnetic body varies based on the shape deformation of the structure disposed on the fluid delivery device.

The parameter value related to the change detection sensor may be a reflexibility of a reflective film provided to the change detection sensor, and a change in the reflexibility of the reflective film may be extracted when the structure contacts one side of the reflective film based on the shape deformation of the structure disposed on the fluid delivery device.

The parameter value related to the change detection sensor may be a frequency of a piezo panel provided to the change detection sensor, and a change in the frequency of the piezo panel may be extracted when the structure contacts one side of the piezo panel based on the shape deformation of the structure disposed on the fluid delivery device.

The parameter value related to the change detection sensor may be a current of a conductor provided to the change detection sensor, and a change in the current of the conductor may be extracted when the conductor disposed in a surrounding region of the structure is open-circuited based on the shape deformation of the structure disposed on the fluid delivery device.

The parameter value related to the change detection sensor provided to the surrounding region of the fluid delivery device may be measured only when fluid flows inside the fluid delivery device.

MODE FOR THE INVENTION

This application claims the benefit of Korean Patent Application No. 10-2013-0090439, filed on Jul. 30, 2013, in the Korean Intellectual Property Office, the disclosure of which is incorporated herein in its entirety by reference.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

The terminology used in the specification will be schematically described, and the embodiments of the present invention will be described in detail.

Although general terms as currently widely used as possible are selected as the terms used in the present invention while taking functions in the present invention into account, they may vary according to an intention of those of ordinary skill in the art, judicial precedents, or the appearance of new technology. In addition, in specific cases, terms intentionally selected by the applicant may be used, and in this case, the meaning of the terms will be disclosed in a corresponding description of the invention. Accordingly, the terms used in the present invention should be defined not by simple names of the terms but by the meaning of the terms and the contents over the present invention.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. In addition, sizes of elements in the drawings may be exaggerated for convenience of explanation. In other words, since sizes and thicknesses of components in the drawings are arbitrarily illustrated for convenience of explanation, the following embodiments are not limited thereto.

In the following examples, the x-axis, the y-axis, and the z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

It will be understood that when a layer, region, or component is referred to as being "formed on," another layer, region, or component, it can be directly or indirectly formed on the other layer, region, or component. That is, for example, intervening layers, regions, or components may be present.

As used herein, the term "and/or" includes any and all combinations of one or more of the associated listed items. Expressions such as "at least one of," when preceding a list of elements, modify the entire list of elements and do not modify the individual elements of the list.

FIGS. 1A and 1B illustrate a fluid occlusion detection apparatus 130 according to an embodiment of the present invention.

As shown in FIG. 1A, the fluid occlusion detection apparatus 130 according to an embodiment of the present invention may include a structure 131 and a change detection sensor 133. However, all the shown components are not mandatory components. The fluid occlusion detection apparatus 130 may be implemented by more or less components than the shown components.

A fluid delivery device 100 according to an embodiment of the present invention may include a fluid reservoir container 110 and/or a fluid delivery passageway 120 for connecting a human body and the fluid reservoir container 110.

The structure 131 is disposed on the fluid delivery device 100 and may be deformed according to pressure. For example, the structure 131 may be at least one selected from the group consisting of a membrane, a tube, a piston, and a bellows but is not limited thereto.

Alternatively, the structure 131 may be disposed on the fluid reservoir container 110 or the fluid delivery passageway 120 for connecting a human body and the fluid reservoir container 110.

For example, the structure 131 may be disposed such that a separate structure (e.g., a silicon film) is mounted on a front portion or side surface of the fluid reservoir container 110, or a structure (e.g., a silicon film) is additionally connected to a front portion of the fluid delivery passageway 120.

The change detection sensor 133 may detect a change in a value related to the change detection sensor 133 according to deformation in a shape of the structure 131 due to an increase in pressure inside the fluid delivery device 100 by fluid occlusion inside the fluid delivery device 100.

FIG. 1B is a side view of FIG. 1, wherein the structure 131 is disposed on the fluid delivery device 100 and the change detection sensor 133 is disposed on a surrounding region of the structure 131 and may detect a value that changes according to deformation in the shape of the structure 131.

FIGS. 2A and 2B illustrate deformation in a shape of a structure due to an increase in pressure inside a fluid delivery device according to an embodiment of the present invention.

As shown in FIG. 2A, when fluid occlusion does not occur inside the fluid delivery device 200a, the shape of the structure 210a disposed on the fluid delivery device 200a is not deformed.

For example, the structure 210a is at least one selected from the group consisting of a membrane, a tube, a piston, and a bellows. When pressure is applied to the structure 210a, the shape of the structure 210a may be deformed.

As shown in FIG. 2B, when fluid occlusion occurs inside the fluid delivery device 200a, the shape of the structure 210b may be deformed due to an increase in pressure inside the fluid delivery device 200a. For example, a membrane of the structure 210b may be swollen.

FIGS. 3A and 3B illustrate a change detection sensor including a capacitor, according to an embodiment of the present invention.

As shown in FIG. 3A, a fluid occlusion detection apparatus 310a according to an embodiment of the present invention may include structures 311a and 132a and the change detection sensor 313a. However, all the shown components are not mandatory components. The fluid occlusion detection apparatus 310a may be implemented by more or less components than the shown components.

As shown in FIG. 3A, when fluid occlusion does not occur inside a fluid delivery device 300a, shapes of the structure 311a disposed on an upper part of the fluid delivery device 300a and the structure 132a disposed on a lower part of the fluid delivery device 300a are not deformed.

For example, the change detection sensor 313a may include the capacitor located on a surrounding region of the structure 311a. In addition, the change detection sensor 313a may further include a capacitance touch sensor and a conductor, such as copper.

The structure 311a disposed on the upper part of the fluid delivery device 300a may be of a material (e.g., silicon, rubber, or the like) which is easy to be physically deformed by pressure, and the structure 132a disposed on the lower part of the fluid delivery device 300a may be of a material (e.g., plastic, metal, or the like) which is difficult to be physically deformed by pressure.

As shown in FIG. 3B, when fluid occlusion occurs inside a fluid delivery device 300b, a shape of a structure 311b disposed on an upper part of the fluid delivery device 300b may be more physically deformed than a shape of a structure 132b disposed on a lower part of the fluid delivery device 300b, due to an increase in pressure inside the fluid delivery device 300b.

Accordingly, the structure 311b disposed on the upper part of the fluid delivery device 300b may contact one side of the capacitor included in the change detection sensor 313b. For example, when fluid (e.g., insulin) inside the fluid delivery device 300b enables to move charges, if the structure 311b (e.g., silicon) containing the fluid (e.g., insulin) contacts one side of the capacitor, charges in the capacitor may be discharged through the structure 311b (e.g., silicon) and the fluid (e.g., insulin). In this case, a fluid occlusion detection apparatus 310b may detect a change in a capacitance of the capacitor through the change detection sensor 313b.

Therefore, the fluid occlusion detection apparatus 310b may detect that fluid occlusion has occurred inside the fluid delivery device 300b, by detecting a change in the capacitance of the capacitor.

FIGS. 4A to 4C illustrate a change detection sensor including a resistor according to another embodiment of the present invention.

As shown in FIG. 4A, when fluid occlusion does not occur inside a fluid delivery device 400a, a shape of a structure 410a disposed on the fluid delivery device 400a is not deformed and a length of the resistor 420a disposed on the structure 410a is not deformed either. The resistor 420a according to an embodiment of the present invention may have a different resistance depending on a shape of the resistor 420a, wherein the resistance may vary according to a length or bending of the resistor 420a based on a type of the resistor 420a.

As shown in FIG. 4B, when fluid occlusion occurs inside a fluid delivery device 400b, a shape of a structure 410b may be deformed due to an increase in pressure inside the fluid delivery device 400b. When the shape of the structure 410b is deformed, the resistor 420b disposed on the structure 410b may also be deformed, and accordingly, a change in a resistance of the resistor 420b may be detected. For example, the resistor 420b may be a strain sensor of which a resistance may vary according to a change in a length of the resistor 420b.

Therefore, a fluid occlusion detection apparatus may detect that fluid occlusion has occurred inside the fluid delivery device 400b, by detecting a change in the resistance of the resistor 420b.

As shown in FIG. 4C, when fluid occlusion occurs inside the fluid delivery device 400c, a shape of a structure 410c may be deformed due to an increase in pressure inside the fluid delivery device 400c. When the shape of the structure 410c is deformed, the resistor 420c disposed on the structure 410c may also be deformed, and accordingly, a change in a resistance of the resistor 420c may be detected. For example, the resistor 420c may be a bending sensor of which a resistance may vary according to bending of the resistor 420c.

Therefore, a fluid occlusion detection apparatus may detect that fluid occlusion has occurred inside the fluid delivery device 400c, by detecting a change in the resistance of the resistor 420c.

FIGS. 5A and 5B illustrate a change detection sensor including a magnetic body 520a or 520b, according to another embodiment of the present invention.

As shown in FIG. 5A, when fluid occlusion does not occur inside a fluid delivery device 500a, a shape of a structure 510a disposed on the fluid delivery device 500a is not deformed and a distance between the magnetic body 520a disposed on the structure 510a and a magnetic field sensor 530a for measuring a magnetic field of a surrounding region of the magnetic body 520a may be constant. For example, the magnetic field sensor 530a according to an embodiment of the present invention may be a Hall effect sensor and/or a lead switch but is not limited thereto.

As shown in FIG. 5B, when fluid occlusion occurs inside a fluid delivery device 500b, a shape of a structure 510b may be deformed due to an increase in pressure inside the fluid delivery device 500b. When a distance between the magnetic body 520b disposed on the structure 510b and a magnetic field sensor 530b according to the deformation in the shape of the structure 510b, a change in a magnetic field of the magnetic body 520b, which is measured by the magnetic field sensor 530b, may be detected.

Therefore, a fluid occlusion detection apparatus may detect that fluid occlusion has occurred inside the fluid delivery device 500b, by detecting a change in the magnetic field of the magnetic body 520b.

FIGS. 6A and 6B illustrate a change detection sensor including a reflective film 620a or 620b, according to another embodiment of the present invention.

As shown in FIG. 6A, when fluid occlusion does not occur inside a fluid delivery device 600a, a shape of a structure 610a disposed on the fluid delivery device 600a is not deformed, and accordingly, a reflexibility of the reflective film 620a interposed between the structure 610a and a detection unit 630a including a light-transmitting unit and a light-receiving unit, which is measured by the detection unit 630a, is constant. In addition, the light-transmitting unit in the detection unit 630a according to an embodiment of the present invention may use an LED device, but power consumption of the LED device may be reduced by coating a color or material for increasing the reflexibility on the reflective film 620a.

As shown in FIG. 6B, when fluid occlusion occurs inside a fluid delivery device 600b, a shape of a structure 610b may be deformed due to an increase in pressure inside the fluid delivery device 600b. In this case, the structure 610b may contact the reflective film 620b according to the deformation in the shape of the structure 610b. In this case, total reflection of the reflective film 620b is not achieved, and accordingly, the intensity of light measured by the light-receiving unit in a detection unit 630b varies due to a light-absorbing material. That is, a reflexibility of the reflective film 620b varies.

Therefore, a fluid occlusion detection apparatus may detect that fluid occlusion has occurred inside the fluid delivery device 600b, by detecting a change in the reflexibility of the reflective film 620b.

FIGS. 7A and 7B illustrate a change detection sensor including a piezo panel 720a or 720b, according to another embodiment of the present invention.

As shown in FIG. 7A, when fluid occlusion does not occur inside a fluid delivery device 700a, a shape of a structure 710a disposed on the fluid delivery device 700a is not deformed and the piezo panel 720a disposed on the fluid delivery device 700a may vibrate at a constant frequency.

As shown in FIG. 7B, when fluid occlusion occurs inside a fluid delivery device 700b, a shape of a structure 710b may be deformed due to an increase in pressure inside the fluid delivery device 700b. For example, when the structure 710b contacts one side of the piezo panel 720b according to the deformation in the shape of the structure 710b, a change in the frequency of the piezo panel 720b may be detected.

Therefore, a fluid occlusion detection apparatus may detect that fluid occlusion has occurred inside the fluid delivery device 700b, by detecting a change in the frequency of the piezo panel 720b.

FIGS. 8A to 9B illustrate a change detection sensor including a conductor 820a, 820b, 920a, or 920b, according to other embodiments of the present invention.

As shown in FIGS. 8A and 9A, when fluid occlusion does not occur inside fluid delivery devices 800a and 900a, a shape of structures 810a and 910a respectively disposed on the fluid delivery devices 800a and 900a are not deformed, and the conductor 820a disposed in a surrounding region of the structure 810a and the conductor 920a disposed on the structure 910a so as to overlap may be in a power supply state since each of the conductors 820a and 920a according to an embodiment of the present invention is formed on a carbon bar and/or a ceramic bar and has conductivity.

As shown in FIGS. 8B and 9B, when fluid occlusion occurs inside fluid delivery devices 800b and 900b, shapes of structures 810b and 910b may be deformed due to an increase in pressure inside the fluid delivery devices 800b and 900b. Each of the structures 810b and 910b may be at least one selected from the group consisting of a membrane, a tube, a piston, and a bellows, which has a film expanding according to applied pressure or has an elastic film.

When the shapes of the structures 810b and 910b expand, a physical force may be applied to the conductors 820b and 920b. For example, each of the conductors 820b and 920b may be formed on a carbon bar which is easy to be broken or a ceramic bar on which a conductor is plated. In this case, the conductor 820b is weak to a physical force, and thus the conductor 820b may break. Alternatively, when the conductor 920b is disposed on the structure 910b so as to overlap the structure 910b in a normal state, the overlapping contact point may be separated due to physical pressure occurring according to a change in a shape of the conductor 920b.

When the conductors 820b and 920b are broken or separated, the conductors 820b and 920b according to embodiments of the present invention may be open-circuited. For example, this case is similar to the principle of a fuse. In other words, by supplying power to a pump circuit in a normal state and cutting off power to the pump circuit as soon as fluid occlusion is detected without a separate additional circuit, an inflow of fluid into a human body may be prevented.

Therefore, a fluid occlusion detection apparatus may detect that fluid occlusion has occurred inside the fluid delivery device 800b or 900b, by detecting a change in a current of the conductor 820b or 920b.

However, the conductor 820b or 920b is physically damaged, and thus, the conductor 820b or 920b may be used for a disposable product.

FIG. 10 is a flowchart of a fluid occlusion detection method according to an embodiment of the present invention.

In operation S100, a parameter value related to a change detection sensor provided to a surrounding region of a fluid delivery device is measured.

The parameter value according to an embodiment of the present invention may be any one of a capacitance of a capacitor, a resistance of a resistor, a magnetic field of a magnetic body, a reflexibility of a reflective film, a frequency of a piezo panel, and a current of a conductor but is not limited thereto.

In addition, according to an embodiment of the present invention, the parameter value related to the change detection sensor provided to the surrounding region of the fluid delivery device may be measured only when fluid flows inside the fluid delivery device to reduce power consumption of a fluid occlusion detection apparatus.

In operation S110, a change in the measured parameter value is extracted based on deformation in a shape of a structure disposed on the fluid delivery device.

According to an embodiment of the present invention, the shape of the structure may be deformed due to an increase in pressure inside the fluid delivery device by fluid occlusion inside the fluid delivery device. For example, the structure may be at least one selected from the group consisting of a membrane, a tube, a piston, and a bellows but is not limited thereto.

In operation S120, fluid occlusion inside the fluid delivery device is detected based on the extracted change in the measured parameter value.

The extracted change in the measured parameter value according to an embodiment of the present invention may be a change in the capacitance of the capacitor when the structure, of which the shape has been deformed due to an increase in the pressure inside the fluid delivery device, contacts one side of the capacitor or a change in the resistance of the resistor when a shape of the resistor is deformed by the structure, of which the shape has been deformed due to an increase in the pressure inside the fluid delivery device.

Alternatively, the extracted change in the measured parameter value according to an embodiment of the present invention may be a change in the magnetic field of the magnetic body when a distance between the magnetic body and a magnetic field sensor varies based on the shape deformation of the structure due to an increase in the pressure inside the fluid delivery device or a change in the intensity of light received by a light-receiving unit when the structure contacts one side of the reflective film based on the shape deformation of the structure due to an increase in the pressure inside the fluid delivery device.

Alternatively, the extracted change in the measured parameter value according to an embodiment of the present invention may be a change in the frequency of the piezo panel when the structure contacts one side of the piezo panel based on the shape deformation of the structure due to an increase in the pressure inside the fluid delivery device or a change in the current of the conductor when the conductor is open-circuited based on the shape deformation of the structure due to an increase in the pressure inside the fluid delivery device.

According to another embodiment of the present invention, the conductor provided in the change detection sensor may be formed on a carbon bar and/or a ceramic bar and may have conductivity in a normal state.

In this case, when the conductor is physically broken according to the shape deformation of the structure due to an increase in the pressure inside the fluid delivery device by fluid occlusion inside the fluid delivery device, the conductor is open-circuited to cut off power to a pump circuit as soon as fluid occlusion is detected without a separate additional circuit, thereby preventing an inflow of fluid into a human body.

All cited references including publicized documents, patent applications, and patents cited in the present invention can be merged in the present invention in the same manner as the shown by individually and concretely merging each cited reference and the shown by generally merging each cited reference in the present invention.

For the understanding of the present invention, reference numerals are disclosed in the exemplary embodiments shown in the drawings, and specific terms are used to describe the exemplary embodiments of the present invention. However, the present invention is not limited by the specific terms, and the present invention may include all components, which can be commonly thought by those of ordinary skill in the art.

The present invention can be represented with functional blocks and various processing steps. These functional blocks can be implemented by various numbers of hardware and/or software configurations for executing specific functions. For example, the present invention may adopt direct circuit configurations, such as memory, processing, logic, and look-up table, for executing various functions under control of one or more processors or by other control devices. Like components of the present invention being able to execute the various functions with software programming or software elements, the present invention can be implemented by a programming or scripting language, such as C, C++, Java, or assembler, with various algorithms implemented by a combination of a data structure, processes, routines, and/or other programming components. Functional aspects can be implemented with algorithms executed in one or more processors. In addition, the present invention may adopt the prior art for electronic environment setup, signal processing and/or data processing. The terms, such as "mechanism", "element", "means", and "configuration", can be widely used and are not delimited as mechanical and physical configurations. The terms may include the meaning of a series of routines of software in association with a processor.

Specific executions described in the present invention are exemplary embodiments and do not limit the scope of the present invention even in any method. For conciseness of the specification, disclosure of conventional electronic configurations, control systems, software, and other functional aspects of the systems may be omitted. In addition, connections or connection members of lines between components shown in the drawings illustrate functional connections and/or physical or circuit connections, and the connections or connection members can be represented by replaceable or additional various functional connections, physical connections, or circuit connections in an actual apparatus. In addition, if there is no concrete use of terms such as "requisite" or "important" to refer a component, that component may not be necessarily required for application of the present invention.

The use of the term "said" or a similar directional term in the specification (in particular, in claims) of the present invention may correspond to both the singular and the plural. In addition, when a range is disclosed in the present invention, inventions to which individual values belonging to the range are applied are included (if there is no disclosure opposed to this), and this is the same as if each of the individual values forming the range is disclosed in the detailed description of the present invention. Finally, for steps forming the methods according to the present invention, if an order is not clearly disclosed or, if there is no disclosure opposed to the clear order, the steps can be performed in any order deemed proper. The present invention is not necessarily limited to the disclosed order of the steps. The use of all illustrations or illustrative terms (for example, and so forth, etc.) in the present invention is simply to describe the present invention in detail, and the scope of the present invention is not limited due to the illustrations or illustrative terms unless they are limited by claims. In addition, it will be understood by those of ordinary skill in the art that various modifications, combinations, and changes can be formed according to design conditions and factors within the scope of the attached claims or the equivalents.

As described above, according to the one or more of the above embodiments of the present invention, by using any one of a capacitor, a resistor, a conductor, a magnetic body, a reflective film, and a piezo panel instead of using an existing LED device to detect fluid occlusion, current consumption may be reduced.

In addition, by supplying power to a pump circuit in a normal state and cutting off power to the pump circuit as soon as fluid occlusion is detected without a separate additional circuit, an inflow of fluid into a human body may be prevented.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

The invention claimed is:

1. A fluid occlusion detection apparatus comprising:
a structure disposed on a fluid delivery device and that is deformed according to pressure; and
a change detection sensor on a surrounding region of the structure, wherein:
    the fluid delivery device comprises a fluid reservoir container and/or a fluid delivery passageway for connecting a human body and the fluid reservoir container,
    the change detection sensor is configured to detect a change in a value related to the change detection sensor due to deformation of a shape of the structure according to an increase in pressure inside the fluid delivery device by fluid occlusion inside the fluid delivery device, and
    the change detection sensor comprises a conductor in the surrounding region of the structure, and is configured to detect a change in a current when the conductor is deformed and open-circuited by a physical force generated by deformation of the shape of the structure due to an increase in the pressure inside the fluid delivery device by fluid occlusion inside the fluid delivery device.

2. The fluid occlusion detection apparatus of claim 1, wherein the structure is disposed on the fluid reservoir container and/or the fluid delivery passageway for connecting the human body and the fluid reservoir container.

3. The fluid occlusion detection apparatus of claim 1, wherein the structure is at least one selected from the group consisting of a membrane, a tube, a piston, and a bellows.

4. The fluid occlusion detection apparatus of claim 1, wherein the conductor is formed on a carbon bar and/or a ceramic bar and has conductivity.

5. A fluid occlusion detection method comprising:
measuring a parameter value related to a change detection sensor provided to a surrounding region of a fluid delivery device;
extracting a change in the measured parameter value based on deformation in a shape of a structure disposed on the fluid delivery device; and
detecting fluid occlusion inside the fluid delivery device based on the extracted change in the measured parameter value, wherein:
    the fluid delivery device comprises a fluid reservoir container and/or a fluid delivery passageway for connecting a human body and the fluid reservoir container,
    a shape of the structure is deformed due to an increase in pressure inside the fluid delivery device by the fluid occlusion inside the fluid delivery device, and
    the parameter value related to the change detection sensor includes current of a conductor provided to the change detection sensor, and a change in the current of the conductor is extracted when the conductor disposed in a surrounding region of the structure is deformed and open-circuited by a physical force generated by the shape deformation of the structure disposed on the fluid delivery device.

6. The fluid occlusion detection method of claim 5, wherein the structure is at least one selected from the group consisting of a membrane, a tube, a piston, and a bellows.

7. The fluid occlusion detection method of claim 5, wherein the parameter value related to the change detection sensor provided to the surrounding region of the fluid delivery device is measured only when fluid flows inside the fluid delivery device.

* * * * *